United States Patent [19]

Bailey

[11] 3,985,539

[45] *Oct. 12, 1976

[54] 4,5-DIHALOPYRROLE-2-CARBONITRILE-CONTAINING TERRESTRIAL AND AQUATIC HEBICIDAL COMPOSITION

[75] Inventor: Denis M. Bailey, East Greenbush, N.Y.

[73] Assignee: Sterling Drug Inc., New York, N.Y.

[ * ] Notice: The portion of the term of this patent subsequent to Feb. 4, 1992, has been disclaimed.

[22] Filed: June 26, 1975

[21] Appl. No.: 590,450

Related U.S. Application Data

[62] Division of Ser. No. 443,740, Feb. 19, 1974, Pat. No. 3,932,458, which is a division of Ser. No. 195,817, Nov. 4, 1971, Pat. No. 3,864,491.

[52] U.S. Cl. ............................ 71/66; 71/67; 71/95
[51] Int. Cl.² ................................. A01N 9/00
[58] Field of Search .......................... 71/66, 95

[56] References Cited

UNITED STATES PATENTS

| | | | |
|---|---|---|---|
| 3,663,701 | 5/1972 | Akerstrom | 424/274 |
| 3,864,491 | 2/1975 | Bailey | 71/66 X |

OTHER PUBLICATIONS

C.A., vol. 69, 1968, p. 59090g.

*Primary Examiner*—Joseph Paul Brust
*Attorney, Agent, or Firm*—William G. Webb; B. W. Wyatt

[57] ABSTRACT

Phytoresponsive and antimicrobial compositions containing, as the active ingredient, a 4,5-dihalopyrrole-2-carbonitrile and methods of combatting microorganisms and plant growth comprising applying an effective antimicrobial or phytotoxic quantity of the active ingredient to a surface to be disinfected or to undesirable plant growth.

20 Claims, No Drawings

4,5-DIHALOPYRROLE-2-CARBONITRILE-CONTAINING TERRESTRIAL AND AQUATIC HEBICIDAL COMPOSITION

This application is a division of my prior, copending application Ser. No. 443,740, filed Feb. 19, 1974, now U.S. Pat. No. 3,932,458, patented Jan. 13, 1976, which in turn is a division of my earlier application Ser. No. 195,817, filed Nov. 4, 1971, copending with application Ser. No. 443,740, and now U.S. Pat. No. 3,864,491, patented Feb. 4, 1975.

This invention relates to the art of combatting microorganisms, for example bacteria and fungi, and undesirable plant growth comprising treating a surface to be disinfected or an area to be cleared of undesirable plant growth with compositions containing, as the active ingredient, a novel 4,5-dihalopyrrole-2-carbonitrile having the formula:

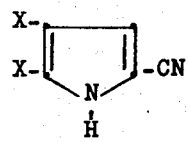  I where X is chlorine, bromine or iodine.

In one of its aspects the instant invention relates to the novel compounds of the above formula I and to methods for the preparation thereof.

In another aspect, the invention relates to compositions for combatting microorganisms containing a 4,5-dihalopyrrole-2-carbonitrile of formula I as the active ingredient in effective antimicrobial amount. The invention also relates to a method of combatting microorganisms comprising treating a surface to be disinfected with a composition containing an effective antimicrobial amount of said active ingredient.

In another of its aspects, the invention relates to aquatic and terrestrial herbicidal compositions containing an effective herbicidal amount of a 4,5-dihalopyrrole-2-carbonitrile of formula I as the active ingredient.

Another aspect of the invention relates to a method of combatting undesirable terrestrial or aquatic plant growth which comprises treating an area to be cleared of such undesirable terrestrial plant growth, or a body of water to be cleared of such undesirable aquatic plant growth, with a composition containing a herbicidally effective amount of a 4,5-dihalopyrrole-2-carbonitrile of formula I as the active ingredient. When used as terrestrial herbidides, the 4,5-dihalopyrrole-2-carbonitrile-containing composition is either sprayed, dusted, or otherwise scattered as described hereinafter over an entire area to be cleared of undesirable vegetation, or alternatively individual plants can be similarly treated. When used as aquatic herbicides to destroy plant growth in a particular body of water, either the 4,5-dihalopyrrole-2-carbonitrile itself, or a composition containing it, is dissolved directly in the body of water in an amount, to be described hereinafter, sufficient to provide a herbicidally effective concentration of the active ingredient in the body of water being treated.

The compounds of formula I are generally prepared by direct halogenation of pyrrole-2-carbonitrile. In the case of the compounds where X is chlorine or bromine, the halogenation is advantageously carried out with the elemental halogen in glacial acetic acid at a temperature from 0° to around 50° C.

The compounds where X is iodine, on the other hand, are advantageously prepared by reaction of pyrrole-2-carbonitrile with a solution of iodine monochloride and sodium or potassium chloride in aqueous acetic acid at a temperature from 20° C. to around 100° C.

Alternatively, the compounds can be prepared from the corresponding 4,5-dihalopyrrole-2-carboxaldehyde by conversion of the latter to the corresponding oxime with hydroxylamine using standard procedures known in the art, and conversion of the oxime to the corresponding nitrile by reaction of the oxime with acetic anhydride at a temperature from 40° to around 100° C. This latter method is illustrated by the following reaction sequence:

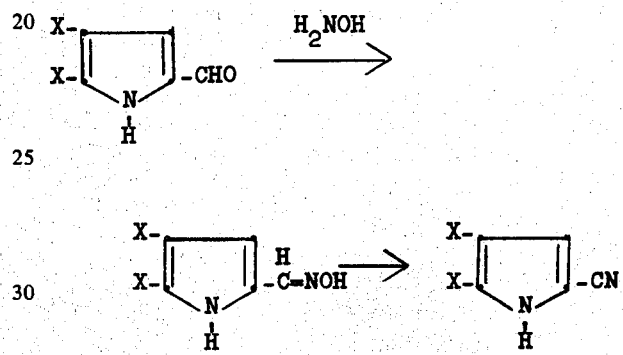

where X has the meanings given above. The 4,5-dihalopyrrole-2-carboxaldehydes in turn are prepared by direct halogenation of pyrrole-2-carboxaldehyde by methods similar to those described above for the halogenation of pyrrole-2-carbonitrile to the corresponding 4,5-dihalopyrrole-2-carbonitrile.

The compounds of the invention are formulated for use as antimicrobial agents by preparing a dilute solution in an organic medium in which the compounds are soluble, for example ethyl alcohol, acetone, dimethylsulfoxide, and the like, and are applied to a surface to be disinfected, or which is susceptible to contamination, by conventional means such as spraying, swabbing, immersion and the like. Alternatively, the compounds can be formulated as ointments or creams by incorporating them in conventional ointment or cream bases, as alkylpolyether alcohols, cetyl alcohol, stearyl alcohol and the like, or as jellies by incorporating them in conventional jelly bases such as glycerin and tragacanth. They can also be formulated for use as aerosol sprays or foams.

The undesired microorganisms against which the instant compounds are effective may be pathogenic or not but whose presence is unwanted and thus include bacteria, fungi, protozoa, algae, and various other forms of microorganisms well-known to microbiology.

The compounds of the invention are formulated for use as either pre-emergent or post-emergent terrestrial herbicides or as aquatic herbicides by mixing the pure active ingredient with conventional pest control and herbicidal adjuvants, modifiers, diluents or conditioning agents so that they may be formulated as solutions, emulsions, dispersions, dusts or wettable powders.

Liquid formulations of the active compounds according to the present invention for direct herbicidal spraying may be made, for example, with water or water emulsions, petroleum fractions, liquid aliphatic or aromatic alcohols, esters, glycols, or ketones and the like. These liquid formulations can be solutions, dispersions, emulsions or wettable powder dispersions and, if needed, may contain surface active agents, e.g., wetting agents, dispersing agents, emulsifying agents and the like, in sufficient amounts to impart the desired characteristics to the formulation.

Aqueous herbicidal formulations, for example, can be made by adding water to emulsion concentrates, pastes or wettable spray powders of the active ingredients. The wetting, emulsifying or dispersing agents may be either anionic, cationic, nonionic or mixtures thereof. Suitable wetting agents are organic compounds capable of lowering the surface tension of water and include conventional soaps such as the water-soluble salts of long-chain carboxylic acids; amine soaps, such as amine salts of long-chain carboxylic acids; sulfonated animal, vegetable and mineral oils; quaternary salts of high molecular weight acids; rosin soaps such as salts of abietic acid, sulfuric acid salts of high molecular weight organic compounds; algin soaps; and simple and polymeric compositions having both hydrophobic and hydrophilic functions.

Herbicidal dusts may be prepared by mixing or grinding the active substance with a solid carrier material such as talc, diatomaceous earth, kaolin, bentonite, calcium carbonate, boric acid, calcium phosphate, wood, flour, cork, dust, carbon, and the like. Scatterable granules may be obtained, for example, by using ammonium sulfate as carrier material. Alternatively, carrier materials may be impregnated with solutions of the active substances in liquid solvents. Powder preparations or pastes which can be suspended in water and used as sprays may be obtained by adding wetting agents and protective colloids. Different forms of application may be better adapted to the various purposes for which the active substances are to be used by the addition of substances which improve dispersion, adhesion, resistance to rain, and penetrative power such as fatty acids, resins, wetting agents, emulsifying agents, glue and the like. Similarly, the biological spectrum may be broadened by the addition of other substances having bactericidal, fungicidal and plant growth regulating properties and also by combination with fertilizers.

Optimum pre- and post-emergent herbicidal action is obtained using the compounds of the invention at application rates from 1.0 to 8.0 pounds per acre, while optimum aquatic herbicidal activity is obtained using a solution concentration of the active ingredient of from about 1.0 to 40 parts per million.

The following examples illustrate the best mode of making and using the instant invention.

EXAMPLE 1

4,5-Dichloropyrrole-2-carbonitrile

To a solution of 33.5 g. (0.47 mole) of hydroxylamine hydrochloride and 67 g. (0.48 mole) of sodium acetate trihydrate in 130 ml. of water was added 40 g. (0.42 mole) of pyrrole-2-carboxaldehyde. The mixture was shaken vigorously for 5 minutes, cooled in a refrigerator for several days, filtered, and dried giving 45.5 g. of pyrrole-2-carboxaldoxime, m.p. 165°–168° C.

The latter was treated with 150 ml. of acetic anhydride, and after the initial exothermic reaction had subsided, the mixture was stirred and heated slowly to reflux for twenty minutes. The mixture was then cooled and poured into 1500 ml. of water, the mixture extracted with diethyl ether, and the combined extracts charcoaled, concentrated and distilled in vacuo, giving a total of 19.0 g. of pyrrole-2-carbonitrile, b.p. 133°–145° C./25 mm.

The latter (10 g., 0.11 mole), dissolved in 40 ml. of glacial acetic acid, was treated slowly with stirring with a solution of 15.6 g. (0.22 mole) of chlorine dissolved in 300 ml. of glacial acetic acid. The mixture was stirred for an hour and a half, concentrated to a small volume in vacuo, the residue dissolved in diethyl ether, and the organic solution washed with aqueous sodium bicarbonate until the aqueous layer was slightly basic. The organic solution was then dried with anhydrous sodium sulfate, concentrated to dryness and the residue recrystallized from a diethyl ether/hexane mixture giving 9.0 g. of 4,5-dichloropyrrole-2-carbonitrile, m.p. 144°–146° C.

EXAMPLE 2

4,5-Dibromopyrrole-2-carbonitrile

A solution of 25 g. (0.099 mole) of 4,5-dibromopyrrole-2-carboxyaldehyde [prepared according to the method of Anderson et al., Can. J. Chem. 43(2), 409–414 (1965)] and 10.5 g. (0.15 mole) of hydroxylamine hydrochloride in 100 ml. of ethanol was heated on a steam bath with stirring for 5 minutes until all solid material had dissolved. The resulting solution was treated with a solution of 10.5 g. of potassium carbonate in 20 ml. of water, heating and stirring was continued for another ten minutes, and the mixture was poured into 500 ml. of water. The solid which separated was collected and dried in a vacuum oven at 60° C. giving 24.0 g. of 4,5-dibromopyrrole-2-carboxaldoxime, m.p. 150°–152° C.

The latter (19 g., 0.07 mole) was dissolved in 100 ml. of acetic anhydride and the mixture heated on a steam bath for 10 minutes. Concentration of the mixture to dryness in vacuo gave a black residue which was dissolved in diethyl ether. The ether solution was dried over sodium sulfate, charcoaled, concentrated to a small volume, and the solid which separated was recrystallized several times from diethyl ether/hexane to give 12.3 g. of 4,5-dibromopyrrole-2-carbonitrile, m.p. 172°–174° C. (uncorr.)

EXAMPLE 3

4,5-Diiodopyrrole-2-carbonitrile

A solution of 9.2 g. (0.10 mole) of pyrrole-2-carbonitrile in 100 ml. of glacial acetic acid was stirred on a steam bath while 45 ml. of a 4.68N aqueous solution of iodine monochloride/sodium chloride was added slowly over a period of about 15 minutes. The mixture was stirred at 50° C. for about 4 hours, and the precipitate which had separated was collected and dissolved in diethyl ether. The organic solution was washed first with 200 ml. of water, then with 400 ml. of saturated aqueous sodium bicarbonate, dried over anhydrous magnesium sulfate, and concentrated to dryness to give a solid residue. Recrystallization of the latter from ethyl acetate/hexane afforded 16.5 g. of 4,5-diiodopyrrole-2-carbonitrile, m.p. 211°–213° C. (uncorr.)

Anti-bacterial and anti-fungal activities for the compounds were established using standard serial dilution techniques as described by Goss and Cimijotti, Applied Microbiology, 16 1414–1416 (1968). The minimum (bactericidal and fungicidal) inhibitory concentrations (MIC) of the compounds thus tested as solutions d against a variety of bacteria including *Staphylococcus aureus*, *Pseudomonas aeruginosa*, *Escherichia coli*, and *Proteus vulgaris* and against such fungi as *Trichophyton mentagrophytes*, *Aspergillus niger*, and *Candida albicans* were found to be in the range from 8.0 to 125 mcg./ml.

Pre-emergence herbicidal activity for the compounds of the invention was established in an initial screening procedure described as follows: Test crop seeds of five different species of plant growth (lima beans, Dent corn, lettuce, mustard and crabgrass, which were selected as representative of the major classes of mono- and dicotyledonous plants) were planted in 8 ×6 ×3 inch flat-bed trays containing 2 to 3 inches of sandy loam soil. Within 24 hours after planting, an aqueous acetone solution of the test compound was sprayed on the soil at a rate of 8 pounds of test agent per acre. The plants were maintained in a greenhouse and watered regularly for 2 weeks, after which time the phytotoxicity of the test compound was recorded by examining individual plant species for percent kill and assigning a vigor rating to the surviving members of the species according to the following scale:

5 = plants normal
4 = slight injury
3 = moderate injury; plants expected to recover
2 = moderate to severe injury; plants not expected to recover
1 = severe injury; plants will not recover.

Untreated control plants were maintained in every test carried out. The results thus obtained using the compounds of Examples 1, 2 and 3 above are given in TABLE A below.

TABLE A

| TEST PLANT SPECIES | Example 1 Vigor | Example 1 %Kill | Example 2 Vigor | Example 2 %Kill | Example 3 Vigor | Example 3 %Kill |
|---|---|---|---|---|---|---|
| Lima Bean | 5 | 0 | 3 a b | 30 | 5 | 0 |
| Dent Corn | 5 | 0 | 4 a | 0 | 5 | 0 |
| Lettuce | | 100 | | 100 | 5 | 0 |
| Mustard | 3 | 0 | 2 | 90 | 5 | 0 |
| Crabgrass | | 100 | 2 | 90 | 5 | 0 | a Stunted
b Desiccation

Using the same test plant species and the same procedure used in the initial pre-emergence herbicidal screening test described above, the compound of Example 1 (4,5-dichloropyrrole-2-carbonitrile) was reevaluated for pre-emergence herbicidal activity at a rate of 8 pounds per acre and submultiples thereof, i.e. 4 pounds/acre, 2 pounds/acre, and 1 pound/acre. The results thus obtained are given in TABLE B below.

TABLE B

| TEST PLANT SPECIES | 1.0 lb/A Vigor | 1.0 lb/A %Kill | 2.0 lb/A Vigor | 2.0 lb/A %Kill | 4.0 lb/A Vigor | 4.0 lb/A %Kill | 8.0 lb/A Vigor | 8.0 lb/A %Kill |
|---|---|---|---|---|---|---|---|---|
| Lima Bean | 3 | 0 | 4 | 0 | | 100 | 2 | 70 |
| Dent Corn | 4 | 0 | 5 | 0 | 4 | 0 | 3 | 0 |
| Lettuce | 4 | 0 | | 100 | | 100 | | 100 |
| Mustard | 4 | 0 | 4 | 0 | 2 | 90 | 2 | 30 |
| Crabgrass | 3 | 0 | 1 | 95 | | 100 | | 100 |

Post-emergence herbicidal activity for the compounds of the invention was established in an initial screening procedure described as follows: Test crop seeds of the same plant species used in the pre-emergence herbicidal tests were planted in 8×6×3 inch shallow flat-bed trays containing 2 to 3 inches of a loam soil. The growth trays were maintained in a greenhouse and watered regularly for approximately two weeks. When the first trifoliate leaves of the bean plants began to unfold, the test plants were removed from the greenhouse and sprayed with an aqueous acetone solution of the test compound at a rate of 8 pounds of the test compound per acre. The plants were maintained in the greenhouse and watered regularly for an additional two weeks, after which time the phytotoxicity of the test compound was recorded by noting the percent kill and assigning a vigor rating to surviving plants as described above. As in other tests described previously, untreated control plants were maintained in every test. The results thus obtained are given in TABLE C below.

TABLE C

| TEST PLANT SPECIES | Example 1 Vigor | Example 1 %Kill | Example 2 Vigor | Example 2 %Kill | Example 3 Vigor | Example 3 %Kill |
|---|---|---|---|---|---|---|
| Lima Bean | | 100 a | | 100 | 2 a | 60 |
| Dent Corn | | 100 a | 3 | 30 a | 4 | 0 |
| Lettuce | | 100 a | | 100 | | 100 |
| Mustard | | 100 a | 2 | 70 | | 100 |
| Crabgrass | | 100 a | | 100 | | 100 | a Desiccation

Using the same test plant species and the same procedure used in the initial post-emergence herbicidal screening test described above, the compound of Example 1 (4,5-dichloropyrrole-2-carbonitrile) was reevaluated for post-emergence herbicidal activity at a rate of 8 pounds per acre and submultiples thereof, i.e. 4 pounds/acre, 2 pounds/acre, and 1 pound/acre. The results thus obtained are given in TABLE D below.

TABLE D

| TEST PLANT SPECIES | 1.0 lb/A Vigor | 1.0 lb/A %Kill | 2.0 lb/A Vigor | 2.0 lb/A %Kill | 4.0 lb/A Vigor | 4.0 lb/A %Kill | 8.0 lb/A Vigor | 8.0 lb/A %Kill |
|---|---|---|---|---|---|---|---|---|
| Lima Bean | 3 | 60 | 2 | 70 | 2 | 70 | | 100 |

TABLE D-continued

| TEST PLANT SPECIES | 1.0 lb/A Vigor | 1.0 lb/A %Kill | 2.0 lb/A Vigor | 2.0 lb/A %Kill | 4.0 lb/A Vigor | 4.0 lb/A %Kill | 8.0 lb/A Vigor | 8.0 lb/A %Kill |
|---|---|---|---|---|---|---|---|---|
| Dent Corn | 3 | 0 | 3 | 30 | 2 | 70 | 2 | 70 |
| Lettuce |  | 100 |  | 100 |  | 100 |  | 100 |
| Mustard | 3 | 20 | 3 | 70 | 2 | 90 | 100 |  |
| Crabgrass | 2 | 90 |  | 100 |  | 100 |  | 100 |

For the purpose of determining the aquatic herbicidal activity of the compounds of the invention, a nutrient solution constituted as follows was prepared:

| Component | Conc. (g/l) |
|---|---|
| $KNO_3$ | 0.202 |
| $Ca(NO_3)_2 \cdot 4H_2O$ | 0.709 |
| $KH_2PO_4$ | 0.136 |
| $MgSO_4$ | 0.120 |
| $CaCl_2 \cdot 2H_2O$ | 0.441 |
| KCl | 0.149 |
| $MgCl_2 \cdot 6H_2O$ | 0.203 |
| Thiamine | 0.0001 |
| Pyridoxine | 0.0008 |
| Nicotinamide | 0.0008 |
| $H_3BO_3$ | 0.0001 |
| $MnCl_2 \cdot 4H_2O$ | 0.0001 |
| $ZnSO_4 \cdot 7H_2O$ | 0.0003 |
| $CuSO_4 \cdot 5H_2O$ | 0.0001 |
| $Na_2MoO_4 \cdot H_2O$ | 0.0001 |
| Iron Versenol (N-carboxymethyl)-N'-(2-hydroxyethyl)-N,N'-ethylene-diglycine iron salt) | 0.005 |

A sufficient quantity of the test compound to provide a concentration of 5 ppm of active ingredient was dissolved in about 800 ml. of the nutrient solution. To this solution was added 25 to 30 duckweed plants (*Lemna minor L.*) and three snails (*Helisoma trivolvis*). The solutions with the plants and snails were maintained throughout the test at 25° C. under artificial light. Twenty-four hours later, the solutions were examined for snail mortality, and nine days later, the percent reduction of growth of the plants, relative to an untreated control, was recorded. The test solutions were also examined for presence of algae, plant growth aberration, and chlorosis. The results thus obtained are given in TABLE E below.

TABLE E

| Example | %Kill | Snails Killed |
|---|---|---|
| 1 | 100 | no |
| 2 | 100 a | — |
| 3 | 100 a | — | a Algicidal

The aquatic herbicidal activity of the compound of Example 1 was reevaluated according to the following procedure: A sufficient amount of the test compound was dissolved in about three liters of tap water in a glass container, and test plants were placed in the aqueous solution. Test plants which normally grow from a lake or stream bottom were first rooted in a 2½ inch flowerpot containing fertilized silt loam/sandy loam soil, and free floating plants were placed randomly in the aqueous solution. The container holding the toxicant solution, test plants and a few snails was placed under artificial light in a growth chamber, maintained at about 25° C., and after periods of 1, 2, 3, and 4 weeks, during which the solution volume in the test containers was maintained, test plants were examined for kill or reduction of growth compared to plants grown in an aqueous, untreated environment. The plants were rated on a scale of 1 to 5 as indicated above, and in addition, the growth of algae, plant aberration, and snail kill were recorded. The results thus obtained are given in TABLE F below, where the initials P., M., E., C., A., D., and W., at the head of the various columns represent respective aquatic plants, purslane, milfoil, elodea, crowfoot, arrowhead, duckweed, and wolffia.

TABLE F

| Concen. (ppm) | Week of test | P. | M. | E. | C. | A. | D. | W. | Snails Dead |
|---|---|---|---|---|---|---|---|---|---|
| 40 | one | 2 | 2 | 2 | 2 | 2 | 2 | 2 | yes |
|  | two | 2 | 2 | 2 | 2 | 2 | 2 | 1 | yes |
|  | three | 1 | 1 | 1 | 1 | 1 | 3 | 2 | yes |
|  | four | 1 | 1 | 2 | 1 | 1 | 3 | 1 | yes |
| 20 | one | 2 | 2 | 2 | 2 | 2 | 3 | 3 | no |
|  | two | 2 | 2 | 2 | 2 | 2 | 3 | 3 | yes |
|  | three | 1 | 1 | 1 | 1 | 1 | 4 | 3 | yes |
|  | four | 1 | 1 | 2 | 1 | 1 | 5 | 3 | yes |
| 10 | one | 2 | 2 | 2 | 2 | 3 | 3 | 3 | no |
|  | two | 1 | 1 | 2 | 2 | 2 | 3 | 2 | yes |
|  | three | 2 | 2 | 2 | 2 | 2 | 3 | 2 | yes |
|  | four | 1 | 1 | 2 | 1 | 2 | 5 | 3 | yes |
| 5 | one | 3 | 4 | 4 | 2 | 4 | 4 | 3 | no |
|  | two | 2 | 3 | 2 | 1 | 2 | 4 | 4 | yes |
|  | three | 2 | 2 | 2 | 2 | 3 | 3 | 4 | yes |
|  | four | 1 | 1 | 2 | 1 | 3 | 4 | 1 | yes |
| 1 | one | 2 | 2 | 3 | 2 | 3 | 1 | 1 | yes |
|  | two | 1 | 1 | 1 | 1 | 1 | 2 | 2 | yes |
|  | three | 1 | 1 | 1 | 1 | 1 | 2 | 2 | yes |
|  | four | 1 | 1 | 1 | 1 | 2 | 2 | 1 | yes |
| 0.5 | one | 5 | 5 | 5 | 5 | 5 | 5 | 5 | no |
|  | two | 5 | 5 | 5 | 5 | 5 | 5 | 5 | no |
|  | three | 5 | 5 | 5 | 5 | 5 | 5 | 5 | no |
|  | four | 5 | 5 | 5 | 5 | 5 | 5 | 5 | no |
| Control | all | 5 | 5 | 5 | 5 | 5 | 5 | 5 | no |

I claim:
1. A terrestrial or aquatic herbicidal composition consisting essentially of a herbicidally effective amount of a 4,5-dihalopyrrole-2-carbonitrile having the formula

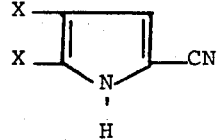

where X is chlorine, bromine or iodine as the active ingredient applied at a terrestrial herbicidal concentration of 1.0 to 8.0 pounds per acre and at an aquatic herbicidal concentration of from 1.0 to 40 parts per million and a conventional carrier especially adapting the composition as a whole to application to areas to be cleared of undesirable terrestrial or aquatic plant growth.

2. A terrestrial herbicidal composition according to claim 1 containing an effective herbicidal amount of 4,5-dichloropyrrole-2-carbonitrile as the active ingredient.

3. A terrestrial herbicidal composition according to claim 1 containing an effective herbicidal amount of 4,5-dibromopyrrole-2-carbonitrile as the active ingredient.

4. A terrestrial herbicidal composition according to claim 1 containing an effective herbicidal amount of 4,5-diiodopyrrole-2-carbonitrile as the active ingredient.

5. A method of combatting undesirable terrestrial plant growth which comprises treating an area to be cleared of such undesirable plant growth with a composition according to claim 1 containing a herbicidally effective amount of a 4,5-dihalopyrrole-2-carbonitrile as the active ingredient.

6. A method according to claim 5 of combatting undesirable terrestrial plant growth which comprises treating an area to be cleared of such undesirable plant growth with a composition containing a herbicidally effective amount of 4,5-dichloropyrrole-2-carbonitrile as the active ingredient.

7. A method according to claim 5 of combatting undesirable terrestrial plant growth which comprises treating an area to be cleared of such undesirable plant growth with a composition containing a herbicidally effective amount of 4,5-dibromopyrrole-2-carbonitrile as the active ingredient.

8. A method according to claim 5 of combatting undesirable terrestrial plant growth which comprises treating an area to be cleared of such undesirable plant growth with a composition containing a herbicidally effective amount of 4,5-diiodopyrrole-2-carbonitrile as the active ingredient.

9. A method according to claim 5 of combatting undesirable terrestrial plant growth which comprises treating an area to be cleared of such undesirable plant growth with a composition containing a 4,5-dihalopyrrole-2-carbonitrile as the active ingredient at an application rate of from 1.0 to 8.0 pounds per acre.

10. A method according to claim 9 of combatting undesirable terrestrial plant growth which comprises treating an area to be cleared of such undesirable plant growth with a composition containing 4,5-dichloropyrrole-2-carbonitrile as the active ingredient at an application rate of from 1.0 to 8.0 pounds per acre.

11. A method according to claim 9 of combatting undesirable terrestrial plant growth which comprises treating an area to be cleared of such undesirable plant growth with a composition containing 4,5-dibromopyrrole-2-carbonitrile as the active ingredient at an application rate of from 1.0 to 8.0 pounds per acre.

12. A method according to claim 9 of combatting undesirable terrestrial plant growth which comprises treating an area to be cleared of such undesirable plant growth with a composition containing 4,5-diiodopyrrole-2-carbonitrile as the active ingredient at an application rate of from 1.0 to 8.0 pounds per acre.

13. A method of combatting undesirable aquatic plant growth which comprises treating a body of water to be cleared of such undesirable plant growth with a composition according to claim 1 containing a herbicidally effective amount of a 4,5-dihalopyrrole-2-carbonitrile as the active ingredient.

14. A method according to claim 13 of combatting undesirable aquatic plant growth which comprises treating a body of water to be cleared of such undesirable plant growth with a composition containing a herbicidally effective amount of 4,5-dichloropyrrole-2-carbonitrile as the active ingredient.

15. A method according to claim 13 of combatting undesirable aquatic plant growth which comprises treating a body of water to be cleared of such undesirable plant growth with a composition containing a herbicidally effective amount of 4,5-dibromopyrrole-2-carbonitrile as the active ingredient.

16. A method according to claim 13 of combatting undesirable aquatic plant growth which comprises treating a body of water to be cleared of such undesirable plant growth with a composition containing a herbicidally effective amount of 4,5-diiodopyrrole-2-carbonitrile as the active ingredient.

17. A method according to claim 12 for combatting undesirable aquatic plant growth which comprises treating a body of water to be cleared of such undesirable plant growth with a composition containing a 4,5-dihalopyrrole-2-carbonitrile as the active ingredient at a concentration of from 1.0 to 40 parts per million.

18. A method according to claim 17 for combatting undesirable aquatic plant growth which comprises treating a body of water to be cleared of such undesirable plant growth with a composition containing 4,5-dichloropyrrole-2-carbonitrile as the active ingredient at a concentration of 1.0 to 40 parts per million.

19. A method according to claim 17 for combatting undesirable aquatic plant growth which comprises treating a body of water to be cleared of such undesirable plant growth with a composition containing 4,5-dibromopyrrole-2-carbonitrile as the active ingredient at a solution concentration of 1.0 to 40 parts per million.

20. A method according to claim 17 for combatting undesirable aquatic plant growth which comprises treating a body of water to be cleared of such undesirable plant growth with a composition containing 4,5-diiodopyrrole-2-carbonitrile as the active ingredient at a solution concentration of 1.0 to 40 parts per million.

* * * * *

UNITED STATES PATENT AND TRADEMARK OFFICE
CERTIFICATE OF CORRECTION

PATENT NO. : 3,985,539
DATED : October 12, 1976
INVENTOR(S) : Denis M. Bailey

It is certified that error appears in the above-identified patent and that said Letters Patent are hereby corrected as shown below:

Face page and column 1, the third line of the title, in each change "Hebicidal to read -- Herbicidal --.

Column 1, line 52, change "herbidides" to read --herbicides--.

Column 1, line 58, after "growth" insert --growing--.

Column 10, line 29, claim 17 change "claim 12" to read --claim 13--.

Signed and Sealed this

Twenty-seventh Day of April 1982

[SEAL]

Attest:

Attesting Officer

GERALD J. MOSSINGHOFF
Commissioner of Patents and Trademarks